United States Patent
Woo

(10) Patent No.: US 11,033,197 B2
(45) Date of Patent: Jun. 15, 2021

(54) APPARATUS FOR MEASURING BIOIMPEDANCE AND ELECTRODE-SIDE BOARD THEREOF

(71) Applicant: InBody Co., Ltd., Seoul (KR)

(72) Inventor: Jong Bum Woo, Yongin-si (KR)

(73) Assignee: InBody Co., Ltd., Seoul (KR)

( * ) Notice: Subject to any disclaimer, the term of this patent is extended or adjusted under 35 U.S.C. 154(b) by 637 days.

(21) Appl. No.: 15/651,586

(22) Filed: Jul. 17, 2017

(65) Prior Publication Data

US 2018/0020945 A1 Jan. 25, 2018

(30) Foreign Application Priority Data

Jul. 22, 2016 (KR) .................. 10-2016-0093283

(51) Int. Cl.
| | | |
|---|---|---|
| *A61B 5/053* | (2021.01) | |
| *A61B 5/318* | (2021.01) | |
| *A61B 5/117* | (2016.01) | |
| *H03H 7/38* | (2006.01) | |
| *A61B 5/00* | (2006.01) | |
| *A61B 5/0537* | (2021.01) | |
| *A61B 5/30* | (2021.01) | |
| *A61B 5/259* | (2021.01) | |
| *A61B 5/276* | (2021.01) | |
| *A61B 5/0531* | (2021.01) | |

(52) U.S. Cl.
CPC .............. *A61B 5/053* (2013.01); *A61B 5/117* (2013.01); *A61B 5/318* (2021.01); *H03H 7/38* (2013.01); *A61B 5/0531* (2013.01); *A61B 5/0537* (2013.01); *A61B 5/259* (2021.01); *A61B 5/276* (2021.01); *A61B 5/30* (2021.01); *A61B 5/6833* (2013.01); *A61B 5/7225* (2013.01); *A61B 2562/182* (2013.01)

(58) Field of Classification Search
CPC ...... A61B 5/053; A61B 5/0537; A61B 5/0531
See application file for complete search history.

(56) References Cited

U.S. PATENT DOCUMENTS

| | | | | |
|---|---|---|---|---|
| 2002/0079910 A1* | 6/2002 | Fukuda | .................... | A61B 5/05 |
| | | | | 324/692 |
| 2004/0054298 A1* | 3/2004 | Masuo | ................. | A61B 5/0537 |
| | | | | 600/547 |

FOREIGN PATENT DOCUMENTS

KR     10-2003-0066709        8/2003

\* cited by examiner

*Primary Examiner* — Puya Agahi
(74) *Attorney, Agent, or Firm* — Daly, Crowley, Mofford & Durkee, LLP

(57) ABSTRACT

A bioimpedance measurement apparatus is provided. The bioimpedance measurement apparatus includes an electrode-side board that is configured to be connected to a current electrode in contact with a body and that includes a current source configured to apply a current to the current electrode. The electrode-side board may be connected via a cable to a board in which a processing circuit configured to process a signal acquired through the electrode-side board and/or a frequency signal generator configured to provide a predetermined frequency signal to the electrode-side board are located.

10 Claims, 5 Drawing Sheets

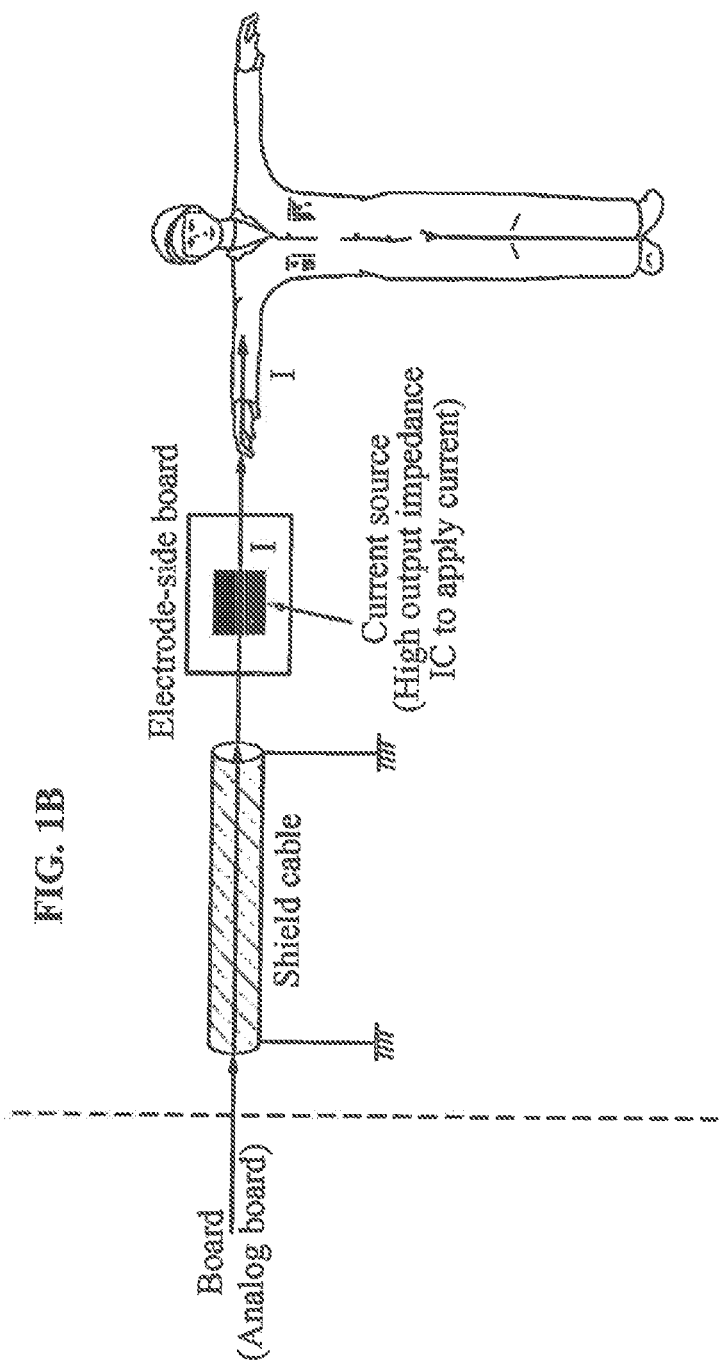

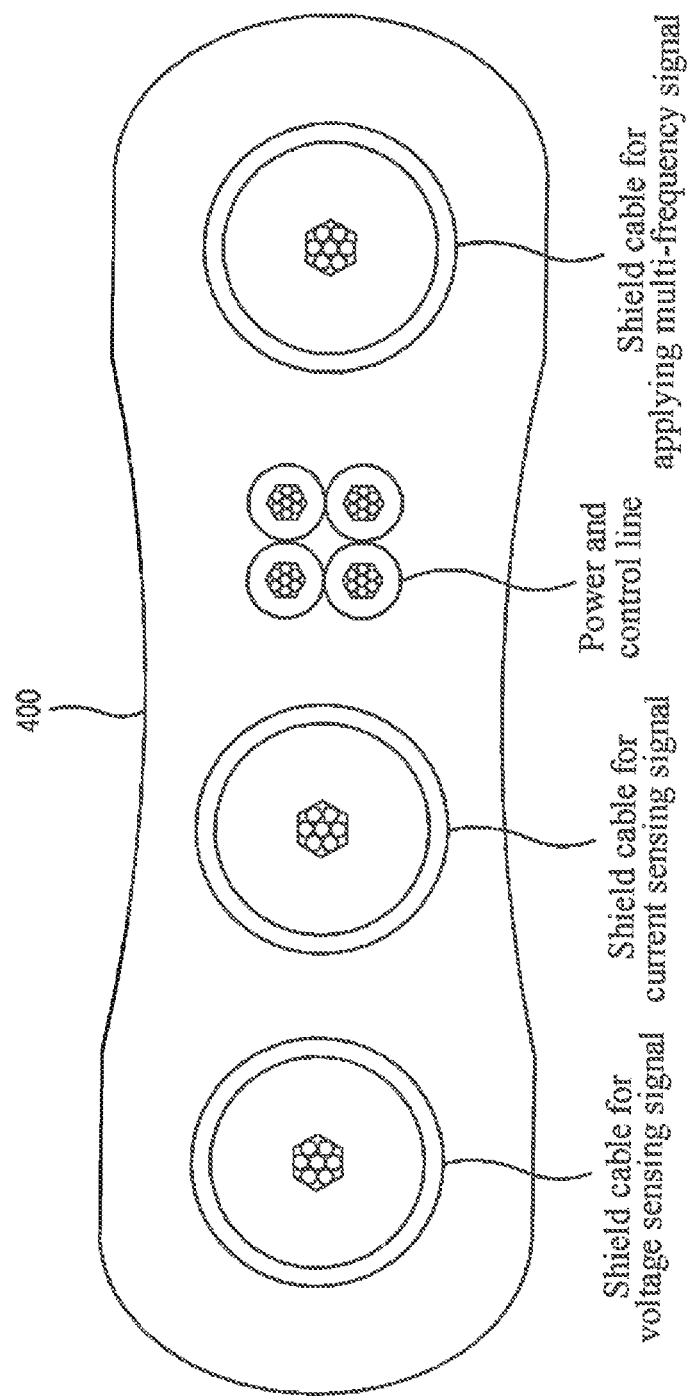

APPARATUS FOR MEASURING BIOIMPEDANCE AND ELECTRODE-SIDE BOARD THEREOF

CROSS-REFERENCE TO RELATED APPLICATION

This application claims the benefit of Korean Patent Application No. 10-2016-0093283, filed on Jul. 22, 2016, in the Korean Intellectual Property Office, the disclosure of which is incorporated herein by reference.

BACKGROUND

1. Field of the Invention

One or more example embodiments relate to a bioimpedance measurement apparatus, and more particularly, to a configuration of an electrode-side board to which an electrode having a bioimpedance is connected.

2. Description of the Related Art

Recently, a bioimpedance measurement apparatus for measuring a bioimpedance is widely used to analyze a characteristic or state of a body as well as a body fat, and the like. For example, due to a difference in a moisture distribution between muscles and fats of a body, a body water content, a muscle mass and a fat mass of a target may be analyzed using a simple and reliable scheme by measuring a bioimpedance of the body.

A bioimpedance measurement apparatus may contact an electrode with a body of a target, may apply predetermined currents through the electrode, and may measure a potential difference between two nodes in a path through which the currents flow, to measure a bioimpedance of the target.

A current that is to be applied to the body to measure the bioimpedance may be generated by a current source in response to a multi-frequency signal. The current may be applied to the electrode via a cable and may flow to the target. However, a high-frequency component of the current generated by the current source may leak while passing through the cable. Actually, a magnitude of a current applied to a current electrode may be reduced due to a loss and leakage of the current through the cable.

In other words, a current transferred to the target may be actually different from the current generated by the current source. When the bioimpedance is measured by measuring the current generated by the current source, the measured bioimpedance may include an error caused by currents that are lost and leaks.

Accordingly, there is a demand for development of a bioimpedance measurement apparatus for accurately measuring a bioimpedance of a target, regardless of a loss and leakage of a current generated by a current source through a cable.

The above-described information is merely to facilitate understanding, and may include information that does not form a part of related arts, including those that may not be presented to those skilled in the art.

SUMMARY

An aspect provides a bioimpedance measurement apparatus that may minimize a loss and leakage of a current applied to a current electrode that is in contact with a body, by disposing a current source configured to apply a current to the current electrode in an electrode-side board.

Another aspect also provides a bioimpedance measurement apparatus that may minimize a loss and leakage of a signal when the signal is transferred between an electrode-side board and a board (for example, an analog board), by connecting the electrode-side board and the board via a shield cable. The electrode-side board may include a current source configured to apply a current to a current electrode, and the board may include a processing circuit configured to process a signal acquired through the electrode-sideboard and a frequency signal generator configured to provide a multi-frequency signal to the electrode-side board.

Still another aspect also provides a bioimpedance measurement apparatus that may measure a bioimpedance of a target regardless of a loss and leakage of a current applied to a current electrode, by disposing, in an electrode-side board, a current source configured to apply a current to the current electrode and a current detection circuit configured to detect a current generated by the current source.

According to an aspect, there is provided a bioimpedance measurement apparatus including an electrode-side board configured to be connected to at least one electrode in contact with a body, the electrode-side board including a current source configured to apply a current to a current electrode among the at least one electrode.

The bioimpedance measurement apparatus may further include a current detection circuit configured to detect a current generated by the current source.

The current detection circuit may be located in the electrode-side board.

The current source may include a driver integrated circuit (IC) used to apply a current.

The current source may be further configured to generate a current that is to be applied to the current electrode in response to a frequency signal being received.

The bioimpedance measurement apparatus may further include a relay configured to be connected between the current electrode and the current source.

The relay may be configured to be open when a current is not applied to the current electrode by the current source.

The electrode-side board may be connected to a board that includes at least one of a processing circuit configured to process a signal acquired through the electrode-side board or a frequency signal generator configured to provide a predetermined frequency signal to the electrode-side board.

The bioimpedance measurement apparatus may further include a transceiver configured to electrically connect the electrode-side board and the board.

At least one of a connection between the processing circuit and the electrode-side board or a connection between the frequency signal generator and the electrode-side board may be performed by the transceiver.

The bioimpedance measurement apparatus may further include a voltage electrode configured to measure a voltage of the body when the voltage electrode is in contact with the body.

A signal acquired by the voltage electrode may be transferred to the board and processed.

At least one of a connection by the transceiver or a connection between the voltage electrode and the board may be performed via a shield cable.

The bioimpedance measurement apparatus may further include an impedance matching circuit for the shield cable.

The impedance matching circuit may include an active device, a resistor and a capacitor.

The impedance matching circuit may be located in at least one end of the shield cable.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects, features, and advantages of the invention will become apparent and more readily appreciated from the following description of example embodiments, taken in conjunction with the accompanying drawings of which:

FIGS. 1A and 1B illustrate a comparison between a bioimpedance measurement apparatus according to a related art and a bioimpedance measurement apparatus according to an example embodiment, in terms of a method of applying a current to a target through a current electrode connected to an electrode-side board to measure a bioimpedance;

FIG. 4 is a diagram illustrating a cable including shield cables used in a bioimpedance measurement apparatus according to an example embodiment.

DETAILED DESCRIPTION

Figure 1A:
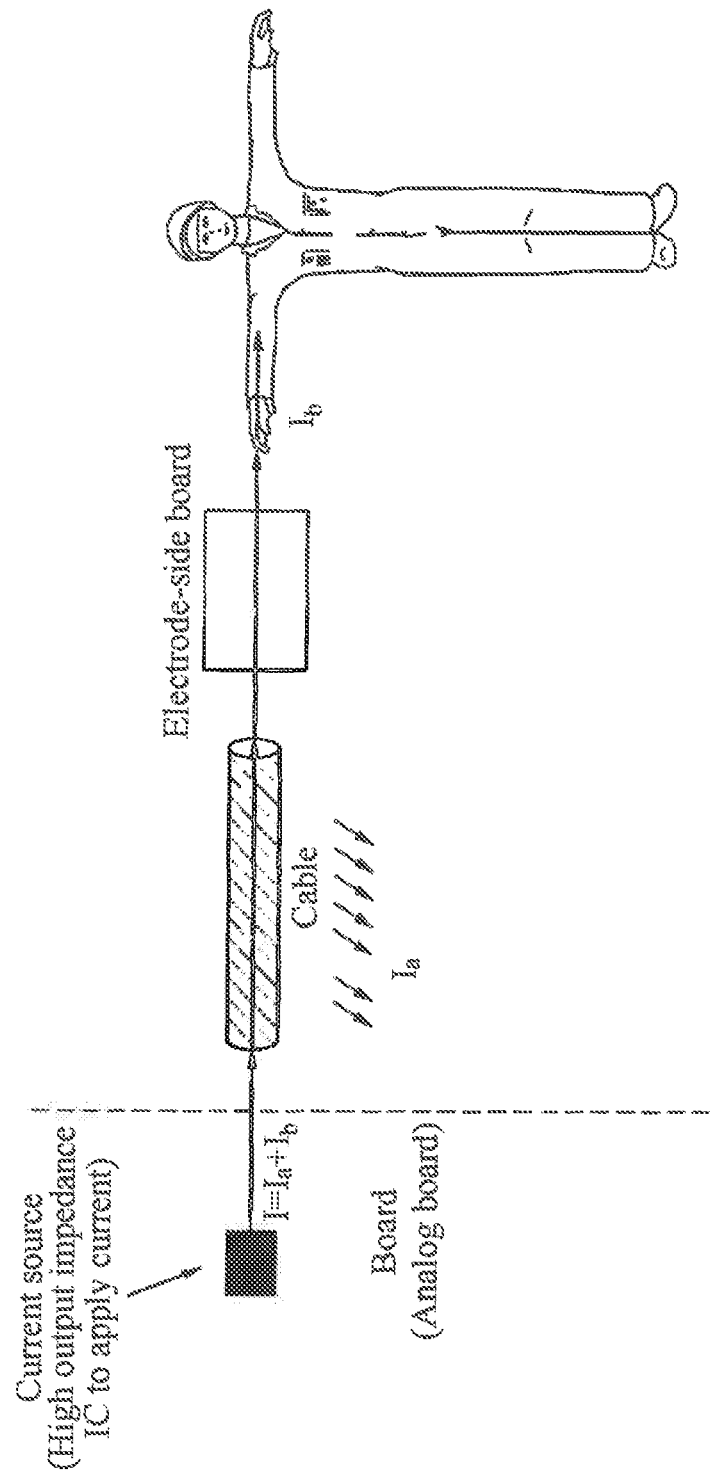

The following structural or functional descriptions of example embodiments described herein are merely intended for the purpose of describing the example embodiments described herein and may be implemented in various forms. However, it should be understood that these example embodiments are not construed as limited to the illustrated forms and include all changes, equivalents, and replacements within the idea and the technical scope of the disclosure.

Although terms of "first," "second," and the like are used to explain various components, the components are not limited to such terms. These terms are used only to distinguish one component from another component. For example, a first component may be referred to as a second component, or similarly, the second component may be referred to as the first component within the scope of the present disclosure.

When it is mentioned that one component is "connected" or "accessed" to another component, it may be understood that the one component is directly connected or accessed to another component or that still other component is interposed between the two components.

As used herein, the singular forms are intended to include the plural forms as well, unless the context clearly indicates otherwise. It will be further understood that the terms "comprises" and/or "comprising," when used in this specification, specify the presence of stated features, integers, steps, operations, elements, components or a combination thereof, but do not preclude the presence or addition of one or more other features, integers, steps, operations, elements, components, and/or groups thereof.

Unless otherwise defined herein, all terms used herein including technical or scientific terms have the same meanings as those generally understood by one of ordinary skill in the art. Terms defined in dictionaries generally used should be construed to have meanings matching contextual meanings in the related art and are not to be construed as an ideal or excessively formal meaning unless otherwise defined herein.

The following example embodiments may be used to recognize an electrocardiogram (ECG) signal of a user. An operation of recognizing an ECG signal of a user may include an operation of verifying or identifying the user by recognizing the ECG signal. An operation of verifying a user may include an operation of determining whether the user is registered. Also, a result obtained by verifying the user may be output as true or false. An operation of identifying a user may include an operation of determining which one of a plurality of registered users corresponds to the user. A result obtained by identifying the user may be output as an identification (ID) of one of the registered users. For example, when the user does not correspond to one of the registered users, a signal indicating that the user is not identified may be output. The example embodiments may be implemented as, for example, a sensor configured to acquire an ECG signal from a body of a user, and a wearable device including a display to output a user authentication result.

Hereinafter, example embodiments will be described in detail with reference to the accompanying drawings. Like reference numerals in the drawings refer to like elements throughout the present disclosure.

FIGS. 1A and 1B illustrate a comparison between a bioimpedance measurement apparatus according to a related art and a bioimpedance measurement apparatus according to an example embodiment, in terms of a method of applying a current to a target through a current electrode connected to an electrode-side board to measure a bioimpedance.

FIGS. 1A and 1B illustrate a method of applying a current to a body of a target, to measure a bioimpedance of the target using the bioimpedance measurement apparatuses.

A bioimpedance measurement apparatus may include a current electrode, a voltage electrode, and a current source that is configured to apply a current to a body through the current electrode. Also, the bioimpedance measurement apparatus may include a current detection circuit configured to detect or measure the current applied by the current source. The bioimpedance measurement apparatus may measure a current applied to the body through the current electrode, and measure a voltage of the body using the voltage electrode, and may calculate a bioimpedance based on the measured current and the measured voltage. For example, the bioimpedance measurement apparatus may apply high-frequency currents generated by the current source to two points of the body, and may measure a potential difference between the two points in a path through which the applied high-frequency currents (that is, a current flowing in the body) flow, to measure a bioimpedance of the target.

FIG. 1A illustrates a current applying method of the bioimpedance measurement apparatus according to the related art. In FIG. 1A, a current source to apply a current to a target is located in a board (for example, an analog board). In the present disclosure, the board may refer to an additional board to an electrode-side board. Also, a current generated by the current source is assumed as "I." The current I may be a current generated in response to a multi-frequency signal obtained by synthesizing multiple frequencies, and may include a current $I_a$ of a relatively high frequency and a current $I_b$ of a relatively low frequency. The current I generated by the current source may be applied to the target via a current electrode connected to the electrode-side board by passing through a cable and the electrode-side board. When the current I passes through the cable, the current $I_a$ may leak out of the cable. The current $I_b$ may be actually applied to the target via the current electrode by passing through the electrode-side board. Also, due to a current that is lost or leaks out of the cable, a magnitude of a current applied to the target via the current electrode may be reduced. Accordingly, when the bioimpedance measurement apparatus detects the current I and when a bioimpedance of the target is measured based on the detected current I, the measured bioimpedance may include an error caused by the leaked current(*current $I_a$.

FIG. 1B illustrates a current applying method of the bioimpedance measurement apparatus according to an example embodiment. In FIG. 1B, a current source to apply a current to a target is located in an electrode-side board instead of a board (for example, an analog board). A current generated by the current source in FIG. 1B may be assumed to be the same as the current I of FIG. 1A. Referring to FIG. 1B, the current I generated by the current source may be applied to the target via a current electrode connected to the electrode-side board, instead of passing through a cable. Accordingly, the loss of the current $I_a$ due to the cable as shown in FIG. 1A may be prevented, and a magnitude of a current may not be reduced. Thus, it is possible to accurately measure a bioimpedance. Also, a shield cable instead of a general cable may be used to connect the electrode-side board and the board, and thus it is possible to minimize a loss of a multi-frequency signal that is received from the board to the current source via the shield cable.

An example of the bioimpedance measurement apparatus in which the current source (for example, a current source to apply a current to a current electrode) is located in the electrode-side board instead of an analog board, will be further described with reference to FIGS. 2, 3 and 4.

Figure 2:
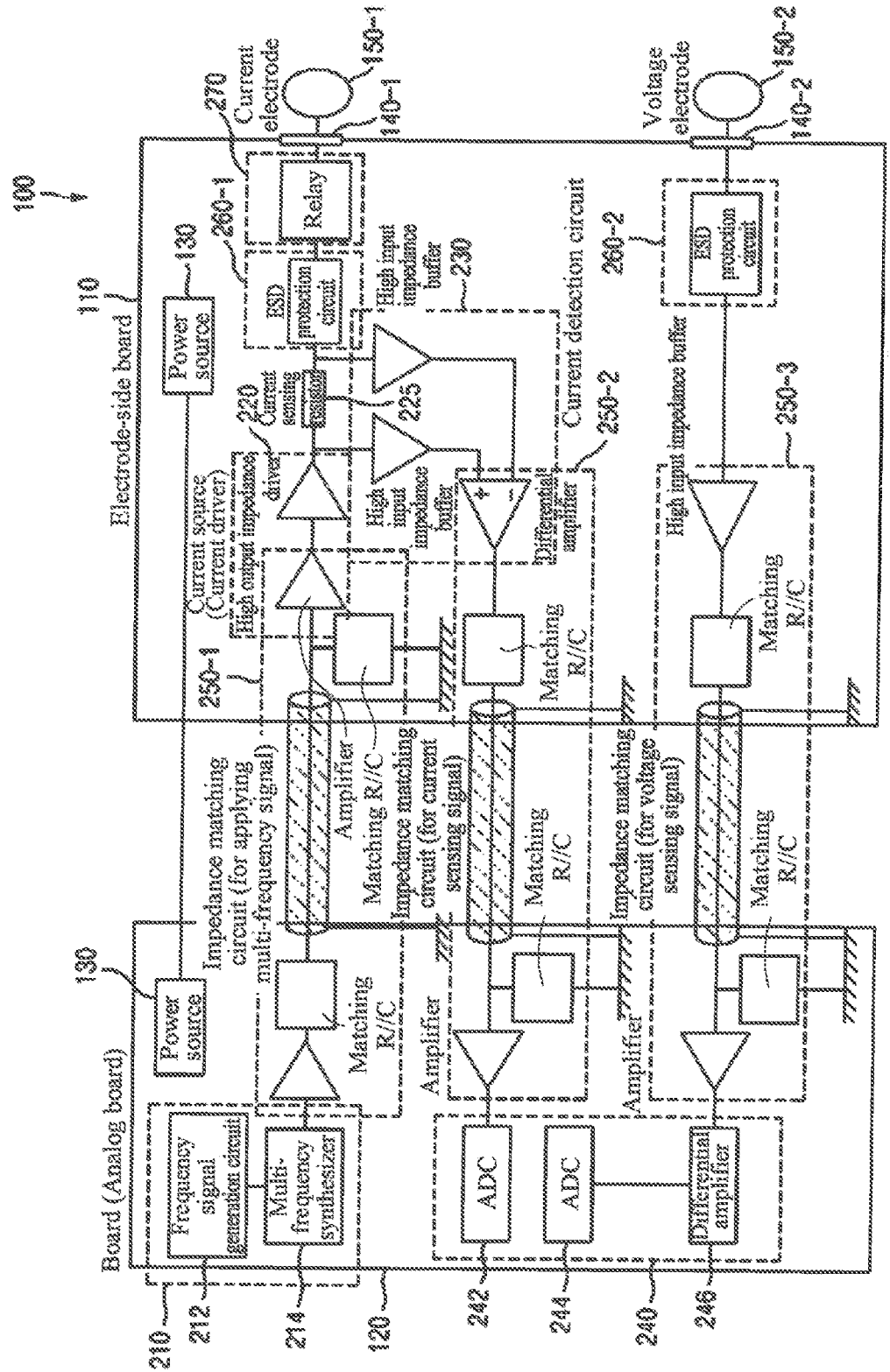
FIG. 2 is a diagram illustrating a bioimpedance measurement apparatus according to an example embodiment.

FIG. 2 illustrates an example of a bioimpedance measurement apparatus 100 according to an example embodiment.

The bioimpedance measurement apparatus 100 may correspond to the bioimpedance measurement apparatus of FIG. 1B in which the current source is located in the electrode-side board.

The bioimpedance measurement apparatus 100 may include an electrode-side board 110 configured to be connected to at least one electrode that is in contact with a body of a target, and a board 120 (for example, an analog board) that is electrically connected to the electrode-side board 110. The electrode-side board 110 and the board 120 may be separate from each other as individual devices. For example, the board 120 may be located as an external device outside the electrode-side board 110. Also, the electrode-side board 110 and the board 120 may be electrically connected to each other via a transceiver.

The transceiver may be located in the electrode electrode-side board 110 and/or the board 120, and may be a device configured to enable a communication (for example, a reception and transmission of data and signals) between the electrode electrode-side board 110 and the board 120 via a wire or wirelessly. In an example, the transceiver may include an antenna for a reception and transmission of signals as a wireless communicator. A wireless communicator of the transceiver may include, for example, a module to implement a wireless communication using a network, such as the Internet, or a module to implement a wireless communication using a Bluetooth technology, however, there is no limitation thereto. Accordingly, the wireless communicator may include a module to implement a wireless communication using all schemes.

In another example, the transceiver may include a cable as a wire communicator.

Although an example in which a transceiver includes a cable is illustrated in FIGS. 1A through 3, the transceiver may include a wireless communicator for a wireless communication between the electrode-side board 110 and the board 120 as described above. In the following description, a cable or a shield cable used as a transceiver may be replaced by a wireless communicator.

When the transceiver includes a wire communicator, the electrode-side board 110 and the board 120 may be connected via a cable to communicate with each other. The cable may include, for example, a shield cable or a screened cable.

When a voltage electrode 150-2 is located outside the electrode-side board 110, the transceiver may include a configuration for a connection between the voltage electrode 150-2 and the board 120.

Also, the bioimpedance measurement apparatus 100 may include a power source 130 to supply power to the electrode-side board 110 and the board 120. Referring to FIG. 2, two power sources 130 may be located in both the electrode-side board 110 and the board 120. Unlike the example of FIG. 2, the power source 130 may be located in either the electrode-side board 110 or the board 120, or may be separate from the electrode-side board 110 and the board 120.

The electrode-side board 110 and the board 120 may be electronic devices that may include an electronic circuit element, a module and a device.

The electrode-side board 110 may include at least one current electrode 150-1 and/or at least one voltage electrode 150-2, or may include connectors 140-1 and 140-2 configured to connect the current electrode 150-1 and the voltage electrode 150-2. Unlike the example of FIG. 2, the voltage electrode 150-2 and the connector 140-2 for the voltage electrode 150-2 may be located in a device or a board other than the electrode-side board 110.

The board 120 may include a processing circuit 240 configured to process a signal acquired through the electrode-side board 110, and a frequency signal generator 210 configured to provide a predetermined frequency signal to the electrode-side board 110. Unlike the example of FIG. 2, either the processing circuit 240 or the frequency signal generator 210 may be located in the board 120.

The electrode-side board 110 may include a current source 220 configured to apply a current to the current electrode 150-1. The current source 220 may be configured as a current driver to generate a current that is to be applied to the body through the current electrode 150-1. The current applied to the current electrode 150-1 by the current source 220 may be detected and used to determine a bioimpedance of the target. The current source 220 may include a driver integrated circuit (IC) used to apply a current. The driver IC may be, for example, a high output impedance driver.

The current source 220 and the frequency signal generator 210 may be connected to each other via a cable, for example, a shield cable. For example, referring to FIG. 2, the frequency signal generator 210 may include a frequency signal generation circuit 212 and a multi-frequency synthesizer 214, and the current source 220 may be connected to the multi-frequency synthesizer 214 via a shield cable. The frequency signal generator 210 may generate or provide a predetermined frequency signal. For example, the frequency signal generator 210 may generate a multi-frequency signal with frequencies in a range of 1 kilohertz (kHz) to 10 megahertz (MHz).

The current source 220 may generate a current that is to be applied to the current electrode 150-1, in response to the predetermined frequency signal being received from the frequency signal generator 210 via the shield cable. For example, the frequency signal generation circuit 212 may generate a signal with frequencies in a range of 1 kHz to 10 MHz, and the signal generated by the frequency signal generation circuit 212 may be synthesized as a multi-frequency signal by the multi-frequency synthesizer 214. The multi-frequency signal may be input as a predetermined frequency signal to the current source 220 via the shield cable, and the current source 220 may generate a current that is to be applied to the current electrode 150-1 in response to an input of the multi-frequency signal.

The current generated by the current source 220 in response to the predetermined frequency signal being received from the frequency signal generator 210 may have a frequency characteristic of the predetermined frequency signal. For example, the generated current may have a multi-frequency characteristic, similarly to the predetermined frequency signal.

The electrode-side board 110 may further include a current detection circuit 230 configured to detect the current generated by the current source 220. The current detection circuit 230 may generate a signal associated with a current based on the detected current. The current detection circuit 230 may be connected to the board 120 via a cable, for example, a shield cable, and may transmit a result obtained by detecting the current generated by the current source 220 as a signal associated with the detected current to the board 120 via the shield cable.

For example, the current detection circuit 230 may be connected to the processing circuit 240 of the board 120 via the shield cable. The processing circuit 240 may process a signal that is associated with the current detected by the current detection circuit 230 and that is received via the shield cable. The processing circuit 240 may include an analog-to-digital converter (ADC) 242. The ADC 242 may receive an analog signal that is associated with the current detected by the current detection circuit 230, and may convert the analog signal into a digital signal. For example, the processing of the signal associated with the current may include converting the signal into a digital signal.

Hereinafter, an operation of the current detection circuit 230 is described in detail. As shown in FIG. 2, a current sensing resistor 225 may be connected between the current source 220 (for example, a driver IC used to apply a current) and the current electrode 150-1. For example, the current detection circuit 230 may include a differential amplifier, and the differential amplifier may be connected to both ends of the current sensing resistor 225. A current (for example, a current signal) flowing in both the ends of the current sensing resistor 225 may be amplified by the differential amplifier, and the amplified current may be a signal associated with a current applied by the current source 220 and may be transmitted to the processing circuit 240 and may be processed. Also, a high input impedance buffer may be connected to each input end of the differential amplifier. By the high input impedance buffer connected to each input end of the differential amplifier, a leakage of a current signal to the differential amplifier may be minimized.

The electrode-side board 110 may further include an electrostatic discharge (ESD) protection circuit 260-1 connected between the current electrode 150-1 and the current source 220. The ESD protection circuit 260-1 may be a static electricity protection circuit, and may be designed to have a predetermined capacitance, for example, a capacitance less than or equal to 1 picofarad (pF). The ESD protection circuit 260-1 may prevent a leakage of a current applied by the current source 220.

Also, the electrode-side board 110 may further include a relay 270 connected between the current electrode 150-1 and the current source 220. As shown in FIG. 2, the relay 270 may be located between the ESD protection circuit 260-1 and the current electrode 150-1. The relay 270 may be located closest to the current electrode 150-1.

The relay 270 may be configured to be open when a current is not applied to the current electrode 150-1 by the current source 220. The relay 270 may include a switch controlled to be in an open state, or may be replaced by the switch.

For example, when a plurality of current electrodes 150-1 are connected to the electrode-side board 110, the relay 270 may be connected to each of the current electrodes 150-1. A relay located close to a current electrode 150-1 to which a current is not applied by the current source 220 among the current electrodes 150-1, may be open. Thus, it is possible to prevent a current from leaking to the current electrode 150-1 to which the current is not applied by the current source 220.

The relay 270 may be designed to have a predetermined capacitance, for example, a capacitance less than or equal to 1 pF.

As described above, the electrode-side board 110 may be configured to be connected to the voltage electrode 150-2 as well as the current electrode 150-1. The voltage electrode 150-2 may be in a contact with a body and may be configured to measure a voltage of the body. Similarly to a side of the electrode-side board 110 connected to the current electrode 150-1, an ESD protection circuit 260-2 may be located in a side of the electrode-side board 110 connected to the voltage electrode 150-2. The above description of the ESD protection circuit 260-1 is also applicable to the ESD protection circuit 260-2, and accordingly is not repeated herein.

A signal acquired or measured by the voltage electrode 150-2 may be transferred to the board 120 and may be processed. For example, the signal acquired by the voltage electrode 150-2 may be processed by the processing circuit 240 of the board 120 that is connected to the voltage electrode 150-2 of the electrode-side board 110 via a shield cable. Also, the processing circuit 240 may include a differential amplifier 246 and an ADC 244. The signal input from the voltage electrode 150-2 to the processing circuit 240 via the shield cable may be amplified by the differential amplifier 246, and the amplified signal may be converted into a digital signal by the ADC 244. The ADC 244 may be integrated with or separate from the above-described ADC 242.

The bioimpedance measurement apparatus 100 may further include a processor configured to perform an operation to determine a bioimpedance of a target based on signals acquired by the electrode-side board 110 and processed, although not shown in FIG. 2. For example, the processor may determine a bioimpedance of a target based on a current signal and a voltage signal that are converted into digital signals by the ADCs 242 and 244.

Also, the processor may control components of the bioimpedance measurement apparatus 100 included in the electrode-side board 110, and components of the bioimpedance measurement apparatus 100 included in the board 120. For example, the processor may control an operation of the relay 270.

For example, the processor may be located in the board 120. In this example, a control signal to control the components of the bioimpedance measurement apparatus 100 included in the electrode-side board 110 may be transmitted from the board 120 to the components in the electrode-side board 110 via a control line (not shown).

The bioimpedance measurement apparatus 100 may further include impedance matching circuits 250-1 through 250-3 for the shield cables that connect the above-described board 120 and electrode-side board 110. Each of the impedance matching circuits 250-1 through 250-3 may include at least one of an active device, a resistor or a capacitor. Each of the impedance matching circuits 250-1 through 250-3 may be located in at least one end of each of the shield cables. As shown in FIG. 2, the impedance matching circuits 250-1 through 250-3 may be 6:1 impedance matching circuits for cables, for example, shield cables. Each of the impedance matching circuits 250-1 through 250-3 may include different devices (or different device values) based on configurations of the shield cables and a configuration of each of the electrode-side board 110 and the board 120 connected to the shield cables. Although a shield cable is included in each of the impedance matching circuits 250-1 through 250-3 as shown in FIG. 2 for convenience, the impedance matching circuits 250-1 through 250-3 may not include a shield cable because the impedance matching circuits 250-1 through 250-3 are configured for impedance matching for the shield cables.

The impedance matching circuits 250-1 through 250-3 will be further described with reference to FIG. 3 below.

The above description of FIG. 1B is also applicable to FIG. 2, and accordingly is not repeated herein.

Figure 3:
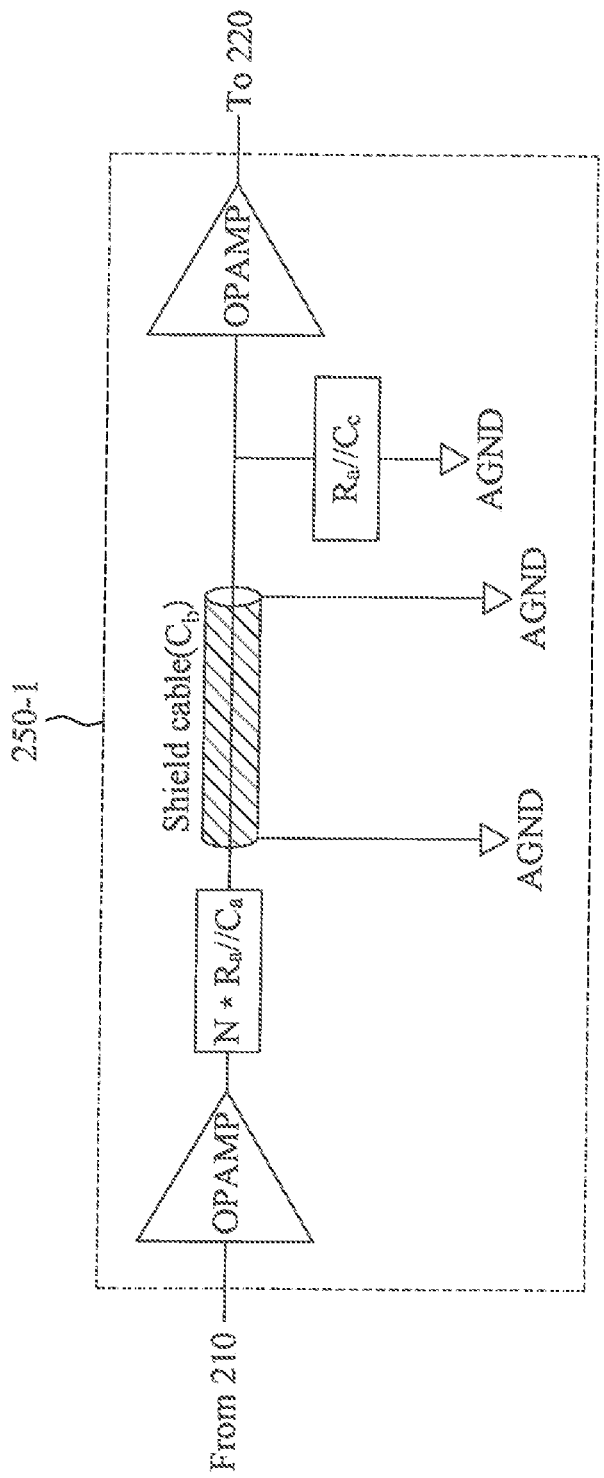
FIG. 3 is a diagram illustrating an impedance matching circuit included in the bioimpedance measurement apparatus of FIG. 2.

FIG. 3 illustrates the impedance matching circuit 250-1 of FIG. 2.

Hereinafter, the impedance matching circuit 250-1 for a shield cable for applying a multi-frequency signal is further described with reference to FIG. 3.

Referring to FIG. 3, the impedance matching circuit 250-1 may include an active device, a resistor and a capacitor. For example, an active device, a resistor and a capacitor in an impedance matching circuit may be located in at least one end of a shield cable.

The active device of the impedance matching circuit 250-1 may include, for example, an operational amplifier (OPAMP). In the impedance matching circuit 250-1, the resistor and the capacitor may be connected to each other in parallel.

For example, in FIG. 3, the impedance matching circuit 250-1 may be configured as a circuit to attenuate a magnitude of a predetermined frequency signal at a ratio of "N:1" to obtain the same gain. The predetermined frequency signal may be, for example, a multi-frequency signal or a frequency signal with a frequency less than or equal to 100 MHz. In this example, N may be a real number greater than or equal to "1."

In FIG. 3, a capacitance value of the shield cable may be assumed as $C_b$. A signal generated by the frequency signal generator 210 may be input to a first OPAMP, may be transmitted to a second OPAMP by sequentially passing through a first impedance matching circuit with $N*R_a//C_a$, the shield cable and a second impedance matching circuit with $R_b//C_c$, and may be output to the current source 220. The first OPAMP and the first impedance matching circuit may be located close to the frequency signal generator 210, and the second OPAMP and the second impedance matching circuit may be located close to the current source 220. Also, a symbol "//" may indicate a parallel connection between devices.

Values of devices in each of the first impedance matching circuit and the second impedance matching circuit, and the capacitance $C_b$ of the shield cable may satisfy Equation 1 shown below.

$$N:1 = N*R_a:R_b = (C_b//C_c):C_a \quad \text{[Equation 1]}$$

For example, each of the first impedance matching circuit and the second impedance matching circuit may include a circuit in which a resistor with a relatively high resistance, for example, 1 megaohm (MΩ), and a capacitor with a relatively low capacitance, for example, 10 pF, are connected in parallel.

The shield cable may be a braid cable with a predetermined length.

Generally, since the capacitance value $C_b$ ranges from 70 pF to 100 pF, it is impossible to transfer a signal with a frequency greater than or equal to 10 MHz without a leakage and attenuation. However, the impedance matching circuit 250-1 for the shield cable may be configured as shown in FIG. 3, and accordingly a capacitance of the shield cable may be designed to be less than 20 pF. For example, an active device (for example, an OPAMP), and a circuit in which a resistor with a resistance of hundreds of kiloohms (KΩ) to a few MΩ and a capacitor with a capacitance less than 20 pF are connected in parallel may be arranged in an input end and output end of the shield cable, and accordingly a magnitude of an input signal up to 100 MHz may be reduced by ⅙, and the same gain of a ⅙ rate may be obtained in all frequency ranges. Also, by the above device arrangement, an output load of the OPAMP(*active device may be reduced, and thus a heating problem of the OPAMP (*active device may be improved.

The above description of the impedance matching circuit 250-1 is also applicable to the impedance matching circuit 250-2 for a shield cable used to apply a current sensing signal and the impedance matching circuit 250-3 for a shield cable used to apply a voltage sensing signal, and accordingly is not repeated herein.

The above description of FIGS. 1B and 2 is also applicable to FIG. 3, and accordingly is not repeated herein.

FIG. 4 illustrates a cable 400 including shield cables used in a bioimpedance measurement apparatus according to an example embodiment.

The cable 400 may correspond to a cable structure including cables (for example, shield cables) used in the bioimpedance measurement apparatus 100 described above with reference to FIGS. 1B through 3.

As described above, in the bioimpedance measurement apparatus 100, shield cables may be used as a multi-frequency signal cable used to apply a multi-frequency signal, a current sensing signal cable, and a voltage sensing signal cable. By using the shield cables, it is possible to prevent electromagnetic interference (EMI) noise from flowing into the shield cables.

Because the shield cables are used as the multi-frequency signal cable as well as the current sensing signal cable and the voltage sensing signal cable, it is possible to shield EMI noise when a multi-frequency signal is applied. Also, it is possible to prevent a multi-frequency signal from leaking out of a cable. For example, even when a cable crosses a human body or metallic object, a leakage of a multi-frequency signal out of the cable may be prevented due to coating of the cable.

Referring to FIG. 4, a shield cable for a voltage sensing signal, a shield cable for a current sensing signal, a power and control line, and a shield cable used to apply a multi-frequency signal may be integrated into a single cable, that is, the cable 400 and may be used. The power and control line may be a cable configured to supply power to the electrode-side board 110 and the board 120 of FIG. 2 and to transfer a control signal.

The above description of FIGS. 1B through 3 is also applicable to the cable 400, and accordingly is not repeated herein.

According to example embodiments, in a bioimpedance measurement apparatus, a current source configured to apply a current to a current electrode may be located in an electrode-side board instead of an analog board, and thus it is possible to apply a current generated by the current source to the current electrode without a loss, and to increase an accuracy of a bioimpedance determination through a current measurement.

Also, according to example embodiments, in a bioimpedance measurement apparatus, shield cables may be used as a cable used to apply a multi-frequency signal, a cable for a current sensing signal, and a cable for a voltage sensing signal, to connect an electrode-side board and an analog board, and thus it is possible to minimize a loss and leakage of a signal when the signal is transferred between the electrode-side board and the analog board, which may lead to an increase in an accuracy of a bioimpedance determination.

The apparatuses (for example, the processor of the bioimpedance measurement apparatus), modules and other components described herein may be implemented using a hardware component, a software component and/or a combination thereof. A processing device may be implemented using one or more general-purpose or special purpose computers, such as, for example, a processor, a controller and an arithmetic logic unit (ALU), a digital signal processor (DSP), a microcomputer, a field programmable gate array (FPGA), a programmable logic unit (PLU), a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciate that a processing device may include multiple processing elements and multiple types of processing elements. For example, a processing device may include multiple processors or a processor and a controller. In addition, different processing configurations are possible, such as parallel processors.

Software executed by a processor to control a function and/or operation of a bioimpedance measurement apparatus according to example embodiments may include a computer program, a piece of code, an instruction, or some combination thereof, to independently or collectively instruct or configure the processing device to operate as desired. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A bioimpedance measurement apparatus comprising:
   an electrode-side board configured to be connected to at least one electrode in contact with a body, the electrode-side board comprising a current source configured to apply a current to a current electrode among the at least one electrode and a current detection circuit configured to detect current between an output of the current source and the current electrode; and
   a board including a frequency signal generator configured to provide a multi frequency signal to the current source via a first shield cable and a processing circuit configured to process a signal acquired through the electrode-side board,
   wherein the current source generates a current having a multifrequency characteristic applied to the current electrode in response to the multi frequency signal
   wherein the processing circuit processes a signal associated with the current detected by the current detection circuit and received via a second shield cable and a signal acquired by a voltage electrode and received via a third shield cable, and
   wherein a bioimpedance of the body is determined using a result processed by the processing circuit.

2. The bioimpedance measurement apparatus of claim 1 wherein the
   current detection circuit comprises a current sensing resistor disposed between the current source and the current electrode and
   wherein the current detection circuit is located in the electrode-side board.

3. The bioimpedance measurement apparatus of claim 1, wherein
   the current source comprises a driver integrated circuit (IC) used to apply the current, and
   the current source is further configured to generate a current that is to be applied to the current electrode in response to a frequency signal being received.

4. The bioimpedance measurement apparatus of claim 1, further comprising:
   a relay configured to be connected between the current electrode and the current source,
   wherein the relay is configured to be open when the current is not applied to the current electrode by the current source.

5. The bioimpedance measurement apparatus of claim 1, further comprising:
   a transceiver configured to electrically connect the electrode-side board and the board,
   wherein at least one of a first connection between the processing circuit and the electrode-side board or a second connection between the frequency signal generator and the electrode-side board is performed by the transceiver.

6. The bioimpedance measurement apparatus of claim 1, further comprising:
the voltage electrode configured to measure a voltage of the body when the voltage electrode is in contact with the body,
wherein the signal acquired by the voltage electrode is transferred to the board and processed.

7. The bioimpedance measurement apparatus of claim 5, wherein at least one of a third connection by the transceiver or a fourth connection between the voltage electrode and the board is performed via a shield cable.

8. The bioimpedance measurement apparatus of claim 6, wherein at least one of a third connection by a transceiver or a fourth connection between the voltage electrode and the board is performed via a shield cable.

9. The bioimpedance measurement apparatus of claim 7, further comprising:
an impedance matching circuit for the shield cable,
wherein the impedance matching circuit is located in at least one end of the shield cable.

10. The bioimpedance measurement apparatus of claim 8, further comprising:
an impedance matching circuit for the shield cable,
wherein the impedance matching circuit is located in at least one end of the shield cable.

* * * * *